United States Patent [19]

Anwer et al.

[11] 4,182,659

[45] Jan. 8, 1980

[54] METHOD OF CONCENTRATING A WATER-CONTAINING GLYCOL

[75] Inventors: Jamil Anwer; Kuldip K. Sud; Karl Wintrup, all of Cologne, Fed. Rep. of Germany

[73] Assignee: Davy International Aktiengesellschaft, Frankfurt, Fed. Rep. of Germany

[21] Appl. No.: 847,410

[22] Filed: Oct. 31, 1977

[51] Int. Cl.² .................................... C07C 29/26
[52] U.S. Cl. .................................. 203/18; 203/49;
203/73; 203/80; 203/DIG. 8; 55/32; 159/47 R;
568/868
[58] Field of Search .................... 203/18, 49, 73, 79,
203/80, 92, 87, 100, 78, 98, 27, DIG. 8;
202/153, 158; 159/23, 29, 17 VS, 47 R; 55/32;
260/637 R

[56] References Cited

U.S. PATENT DOCUMENTS

| | | | |
|---|---|---|---|
| 2,367,695 | 1/1945 | Spiselman | 203/18 |
| 2,510,548 | 6/1950 | Brunjes | 203/18 |
| 3,370,636 | 2/1968 | Francis, Jr. et al. | 203/18 |
| 3,824,177 | 7/1974 | Honerkamp et al. | 203/18 |
| 3,841,382 | 10/1974 | Gravis et al. | 203/18 |
| 4,010,065 | 3/1977 | Alleman | 203/18 |

*Primary Examiner*—Wilbur L. Bascomb, Jr.
*Attorney, Agent, or Firm*—Bernard & Brown

[57] ABSTRACT

Water-containing glycol is heated first at atmospheric or superatmospheric pressure to partially remove water and concentrate the glycol and is then heated at subatmospheric pressure to further concentrate the glycol.

13 Claims, 1 Drawing Figure

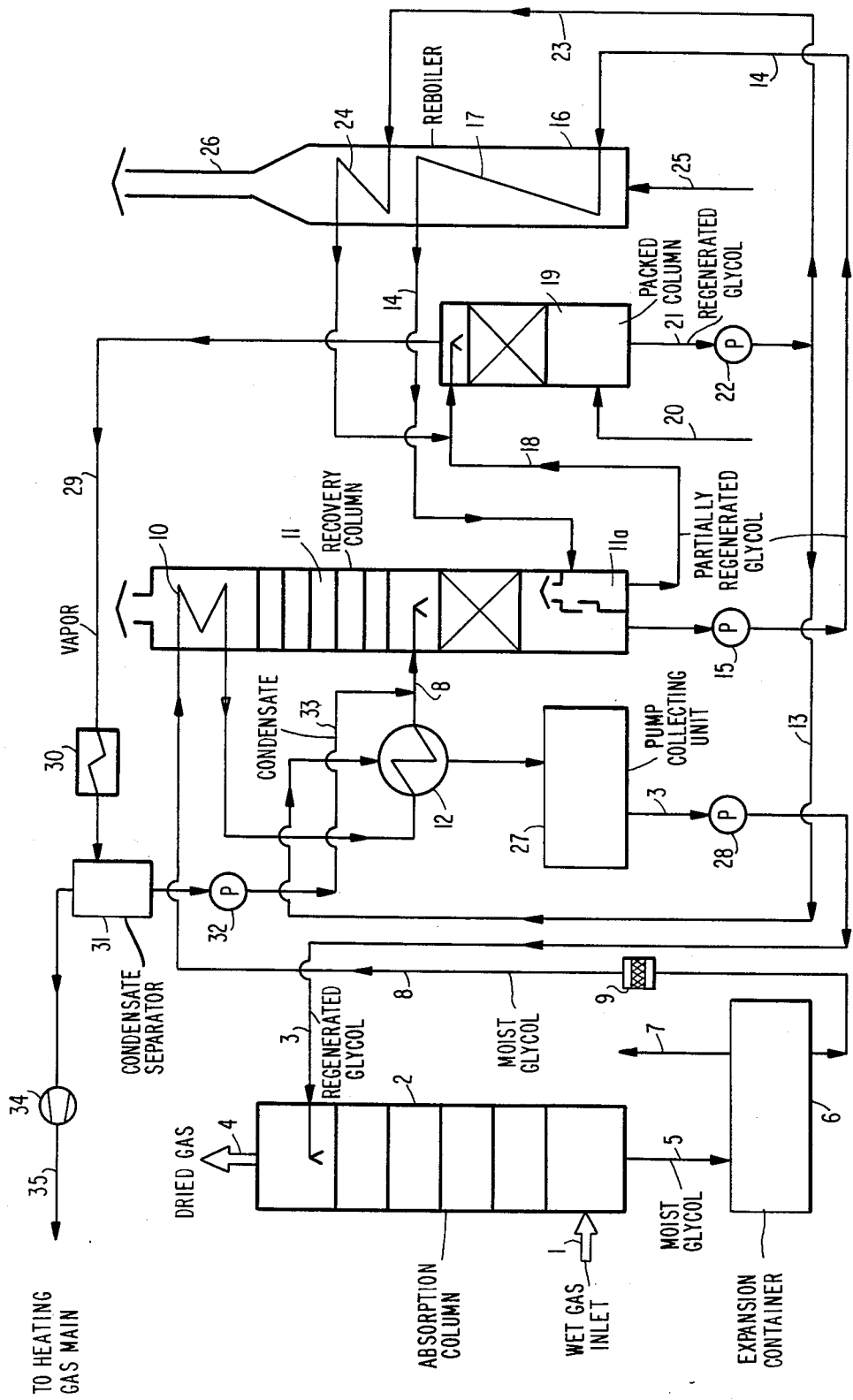

METHOD OF CONCENTRATING A WATER-CONTAINING GLYCOL

The invention relates to a method of reconcentrating a water-containing glycol which is used for drying gas by heating at normal pressure or at an increased pressure in a first stage and by further concentrating the glycol which has been partially concentrated in the first stage at a pressure of less than 1 atmosphere in a second stage.

When gases are dried, particularly natural gas, with a glycol, water vapour is absorbed from the gas, thereby producing a water-containing glycol, from which the water must be removed for the purpose of enabling re-use of the glycol for drying gas. The water-containing glycol is therefore usually heated subject to normal pressure, the greater part of the water vaporising and being separated, and a concentrated glycol, having a low water content, is obtained and is returned into the gas-drying stage. Heating the wet glycol at normal pressure does not enable the glycol to undergo a large measure of dehydration; only a dehydration of up to about 90.0% is possible owing to the restriction of the heating temperature (about 210° C. in the case of triethylene glycol). Higher heating temperatures lead, over long periods of operation, to a partial thermal decomposition of the triethylene glycol, so that the advantage of the higher reconcentration is lost due to the increased cost of replacing the glycol. However, there is an incentive to further increase the concentration of the glycol because the moisture content of the gas dried with glycol is reduced with increasing the concentration of the glycol.

Thus, it is for example possible—when using a 99.9% triethylene glycol instead of a 99% triethylene glycol, and with a contact temperature with the gas to be dried of 20° C.—to reduce the dew point of the gas from about −20° C. to about −40° C.

It is known to effect reconcentration in vacuo because in this way, and with all other conditions unaltered, a higher concentrated glycol can be obtained than is the case under normal pressure. On the other hand, it is also possible to regenerate glycol at a lower temperature and thus prevent decomposition of the glycol. In cases where the glycol is regenerated in vacuo all the water evaporated from the glycol must be condensed, and a large condenser is required for this. Also, the vacuum pump must be dimensioned for all the uncondensible gases which are dissolved in the glycol.

Finally, a two-stage reconcentration of the glycol is known in which a preliminary concentration is carried out thermally in the first stage at normal pressure or at a somewhat increased pressure, and a further concentration is achieved, in the second stage, by expanding into a low-pressure container (U.S. Pat. No. 3,824,177). The condenser and the vacuum pump can be given smaller dimensions, corresponding to the concentration step, in the vacuum stage. However, the reconcentrated glycol obtained in this way still contains a few tenths of one percent of water and does not satisfy the requirements expected of the dew point of the dried gas, particularly in areas having a cold climate. A further drawback of this mode of operation is that the regenerated glycol cools too far, in the vacuum stage, through the expansion and through evaporation of the water, so that a fine regeneration is not possible.

Underlying the invention is the object of regenerating the glycol which has been used up, and which contains water, to a glycol content of about 99.9%. At the same time only a minimum of equipment has to be provided for maintaining the vacuum and for condensing the vapour.

According to the invention this object is achieved—in the case of a method for reconcentrating a water-containing glycol, used for drying gas, by heating at normal pressure, or at an increased pressure, in a first stage, and by further concentrating the glycol, which has been partially concentrated in the first stage, at a pressure of less than 1 atm in a second stage—by, in the second stage, holding the glycol at a temperature in the range of 140° C. to 200° C. by heating. Through the heating of the second stage proposed according to the invention it is ensured that a cooling of the regenerated glycol will not take place in consequence of the expansion and of the evaporation of water and glycol. Such cooling would prevent the glycol from being sufficiently dehydrated as is required for achieving the object underlying the invention, as the water content of the boiling glycol, which is to be regenerated, increases, with decreasing temperature, in equilibrium and at a predetermined pressure. When the glycol concentration is increased in two stages—first of all, in a first regeneration stage, subject to atmospheric pressure or a somewhat increased pressure, water is expelled and a fine regeneration subsequently occurs in a second stage and in the manner proposed according to the invention—the fine regeneration only has to be dimensioned for the residual concentration taking place in this stage. Accordingly, the fine regeneration stage only requires a small outlay in equipment, particularly in connection with dimensioning the vacuum pump and the condenser, arranged upstream of the latter, and can be provided as an addition to single-stage plants, which operate under normal pressure and already exist, or have to be specially set up for the purpose. The concentration takes place, in the first stage, from the starting concentration (which is, for example, 92 to 95% by weight of glycol) to about 99.0% and, in the second stage, from this concentration to over 99.95% by weight of glycol. Accordingly, on the basis of this typical example, 85% of the water to be expelled is removed in the first stage, and only 16% of the water is removed from the glycol in the second stage.

The glycol used is preferably diethylene glycol or triethylene glycol, in particular triethylene glycol. When triethylene glycol is used, the temperature of the second stage is preferably held in the range from 175° to 195° C. and, when diethylene glycol is used, this temperature is preferably held in the range from 160° to 180° C. When other glycols are used, e.g. tetraethylene glycol, the regenerated glycol is held, in the second stage and by heating, at a temperature which lies, in the case of the degree of vacuum selected, between the boiling temperature of the 99% glycol and of the 100% glycol.

According to a preferred embodiment of the invention, the reconcentrated glycol is drawn from the base of the second stage, a part-current of this reconcentrated glycol is heated in a heat exchanger and is returned to the second stage. Due to this heating of the circulated part-current, the temperature in the second stage is held within the above-indicated range.

The heated-part-current is, either immediately or after being combined with the partially regenerated glycol flowing from the first to the second stage, expanded into the gas chamber of the second stage.

Preferably, part of the partially concentrated glycol from the first stage, and part of the concentrated glycol from the second stage, are each pased through a respective heat exchanger, both heat exchangers being heated with the same combustion gas. Thus, in this embodiment, which is particularly suitable for large plants, only one combustion furnace is required for both stages; conveniently, the combustion gas first of all heats the heat exchanger through which the partially-concentrated glycol flows, and then heats the heat exchanger through which the concentrated glycol from the second stage flows. The fuel may for example be constituted by a heating gas, e.g. dried natural gas or the flash gas which is released on expansion of the wet glycol obtained in the absorption stage. The part of the partially-concentrated glycol which has not circulated through the heat exchanger is delivered to the second stage and is expanded either in the second stage or on the way thereto, while the other part of the concentrated glycol from the second stage is returned, after sufficient cooling, to the gas-drying stage.

According to a further preferred embodiment of the invention stripping gas is fed to the second stage for supporting the removal of water. Conveniently, the stripping gas may be guided into the base of the second stage and be guided in countercurrent to the partially-regenerated glycol introduced into this stage. Through the preferred countercurrent contact of the stripping gas with the partially-regenerated glycol, the partial pressure of the water vapour above the glycol is reduced in an effective way by accelerated removal of the water vapour. Owing to this equilibrium shift additional water vaporises from the glycol, as a result of which a very small residual water content remains behind in the liquid phase. This technique is very effective, particularly in countercurrent, for example if the partially-regenerated glycol is delivered to the top part of a column and if the stripping gas is introduced into the base of the column. Surprisingly, it has been found that the infeed of stripping gas to the vacuum stage is appreciably more effective than in the first stage, operating under normal pressure or at an increased pressure, that is to say the water content of the glycol can, for one and the same contact or impingement of the stripping gas, be lowered to an appreciably greater extent if the stripping gas is not fed to the atmospheric regeneration stage but to the regeneration stage operating in vacuo. It may be found appropriate to use dried natural gas as stripping gas, as the gas discharged from the second stage is in any case delivered to the heating gas main. The second stage may be heated with preheated stripping gas. However, generally speaking, heating carried out exclusively with warm stripping gas will not suffice, so that an additional heating is required, e.g. the above-mentioned heat exchange with a combustion gas.

Conveniently, concentration of the glycol in the second stage is carried out in a packed column. The increased interface, thus obtained, between the gas phase and the liquid phase favours, in comparison with an empty tower, the transfer of water into the gas phase and, hence, the speed of the glycol regeneration. Naturally, other columns may be used which ensure a good exchange of material between liquid and gaseous phases.

According to the preferred embodiment of the invention, a pressure within the range of 0.13 to 0.66 atm is used in the second stage, preferably within the range of 0.33 to 0.46. By contrast, the pressure in the first stage preferably amounts to 1.0 to 1.3 atm; for example the pressure may be 1 atm at the head of the first stage and 1.2 atm in the base of the first stage.

According to the preferred embodiment of the method according to the invention the vapour, which contains water vapour, and which proceeds from the second stage, is cooled by heat exchange and is partially condensed, the condensate being returned to the first concentration stage. The vapour consists of water vapour, glycol vapour, and also of residual gaseous hydrocarbons released from the partially regenerated glycol, and possibly of the stripping gas used. The greater part of the glycol vapour and part of the water vapour are condensed from the vapour in a manner corresponding to the partial pressures and in dependence on the operating vacuum and on the condensation temperature. The glycol/water mixture obtained as condensate is, together with the water-containing glycol from the gas-drying stage, returned to the first stage, so that the amount of glycol vaporised in the second stage is not lost. Conveniently, the non-condensed component of the vapour is delivered as heating gas, as we are substantially only concerned here with hydrocarbon gas.

The invention will now be described in greater detail with reference to the drawing, which is in the form of a flow diagram of a plant for carrying out the method according to the invention.

A stream of natural gas to be dried is fed at 1, to an absorption column 2, which is acted on, in countercurrent, with regenerated glycol introduced through ducts 3. The dried natural gas is drawn off, through ducts 4, at the head of the column 2. Absorption takes place, for example at a temperature of 20° C., and subject to a pressure of 38 atm. The glycol, charged with water, is drawn off, through duct 5, from the base or well of the absorption column 2 into the expansion container 6, in which it is expanded to (for example) 5 atmospheres. Part of the hydrocarbon gases absorbed in the absorption column 2 escape from the moist glycol. The hydrocarbon gases are drawn off, through duct 7, from the expansion container 6 and may be re-used as heating gas. The moist glycol then passes through duct 8, in which the glycol filter 9 is arranged, and thence through the dephlegmator 10 of the first regeneration (recovery) column 11, whence it passes to a heat exchanger 12 in which the glycol is preheated to about 170° C. with regenerated glycol introduced through duct 13.

The preheated, moist glycol then passes to the centre part of the recovery column 11, which operates subject to atmospheric pressure and in whose base or well a temperature of 175° to 200° C., and a pressure of 1.2 atmospheres are prevalent; at the head of column 11 a temperature of 90° to 110°, and a pressure of 1 atmosphere, are effective. The main part of the water content of the moist glycol is expelled in column 11 and escapes to the outside atmosphere at the head of the column. For maintaining the temperature in the column 11 a part of the partially recovered product of the base or well of the column 11 is drawn off through duct 14, in which pump 15 is located, passes through a heat exchanger 17 arranged in the reboiler 16, and is returned to the base of column 11. In heat exchanger 17 the temperature of the partially concentrated glycol is increased (for example) from 175° C. to 200° C. The glycol which has thus been heated and partially concentrated passes, in the base of column 11, into a divided-off chamber 11a, while the part-current, led from the base of column 11 to heat exchanger 17, is drawn off outside this chamber 11a, so that direct mixing of the cooler glycol and the heated glycol cannot take place in the base of column 11.

Within chamber 11a a second (part-) current of the partially regenerated glycol is drawn off, through duct 18, from the base of the regeneration column 11, and passed to a packed column 19, to which a condition of vacuum is applied. The expansion of the pressure prevalent in column 11 to the pressure prevalent in column 19 takes place through an expansion valve (not shown) present in duct 18 or through a flow-constricting means (choke) at the head of column 19. At the same time a small quantity of stripping gas is fed, through duct 20, to the base of column 19. The completely regenerated, highly concentrated glycol is drawn off, through duct 21, from the base of column 19 and is returned—by pump 22 and partially through duct 23, in which a heat exchanger 24 is arranged—to duct 18. The heat exchanger 24 is also arranged in the reboiler 16, to which fuel, e.g. heating gas, is fed through duct 25. The combustion gases leave the reboiler 16 through flue 26.

When triethylene glycol is to be concentrated, the vacuum column 19 is maintained, for example, at a pressure of 300 mm Hg and at a temperature of about 180° to 200° C. The part-current circulated through duct 23 is heated in heat exchanger 24 from 180° C. to about 200° C. The glycol expanded in column 19 transfers almost all the water which it still contains to the gas phase due to the expansion and to contact with the stripping gas, a small part of the glycol vaporising. The regenerated glycol drawn off through duct 21 is suitable for being returned to the absorption column 2 and is passed through duct 13 to heat exchanger 12, where it gives up at least part of its heat to the aqueous glycol flowing through the regeneration column 11. This glycol then reaches the pump collecting unit 27, from which it is returned, by means of pump 28 and through duct 3, to the column 2.

The vapour leaving the head of the vacuum column 19 reaches, via ducts 29, the dephlegmator 30, in which the greater part of the glycol vapour and part of the water vapour condense. The condensate is collected in the condensate separator 31, and is returned, from separator 31 and through duct 33, to the regeneration column 11 by means of pump 32. The non-condensed component of the vapour is sucked off by the vacuum blower 34 and delivered, through duct 35, to the heating gas main (not shown).

COMPARISON EXAMPLE 100,000 Nm$^3$/h were treated with triethylene glycol at a pressure of 50 atm and at a temperature of 30° C. in a drying plant. The glycol was regenerated at 200° C. and at atmospheric pressure. The triethylene glycol concentration at the outlet of the regeneration stage was 98.5% by weight. It was possible to dry the natural gas to a dew point of −10° C. with the thus-concentrated glycol. Thus, the dew point was lower by 40° C. The dehydrated triethylene glycol left the absorber of the drying plant with a concentration of 97.3% by weight in the case of a circulation rate of triethylene glycol of 3200 kg/h.

EXAMPLE 1

100,000 Nm$^3$/h of the same natural gas as used in the case of the comparison example were again treated with 3200 kg/h triethylene glycol. The triethylene glycol was regenerated in a two-stage plant, constructed and arranged according to the invention, as shown in the flow diagram. In the first regeneration column the glycol was concentrated—at a glycol temperature of 200° C. and subject to atmospheric pressure—to 98.5% by weight. This partially-concentrated triethylene glycol was then expanded to 400 mm Hg in a vacuum column. The temperature in the base of the vacuum column was held at 190° C. through circulating the product of the base of the vacuum column through a heat exchanger. The concentration of the triethylene glycol at the outlet of the vacuum column amounted to 99.1% by weight. It was possible to dry the natural gas, with this triethylene glycol, to a dew point of −17° C., this corresponds to a lowering of the dew point of 47° C.

EXAMPLE 2

Again, 100,000 Nm$^3$/h of the same natural gas (as used in the comparison example) were treated with 3200 kg/h triethylene glycol. The triethylene glycol was regenerated in a two-stage drying plant constructed and arranged according to the invention, as shown in the flow diagram. In the first regeneration column the glycol was concentrated to 98.5% by weight at a glycol temperature of 200° C. and at atmospheric pressure. This partially-concentrated triethylene glycol was then expanded to 400 mm Hg in a vacuum column and stripped with 20 Nm$^3$ gas/m$^3$. The temperature in the base of the vacuum column was held at about 190° C. by circulating the product of the base of the vacuum column through a heat exchanger. The concentration of triethylene glycol at the outlet of the vacuum column was 99.7% by weight. It is possible, with this triethylene glycol, to dry the natural gas to a dew point of −30° C., corresponding to a dew point lowering of 60° C.

It is claimed:

1. A method of concentrating a water-containing glycol to a glycol concentration of at least about 99 weight percent comprising heating the glycol at atmospheric pressure or at superatmospheric pressure in a first stage of vaporize a major portion of the water from said glycol to thereby partially concentrate the glycol, withdrawing the partially concentrated liquid glycol and a water-containing vapor phase as separate streams from said first stage, further concentrating the partially concentrated liquid glycol in a column forming a second stage by vaporizing water from said glycol at a pressure of less than 1 atmosphere while heating said second stage to maintain a temperature therein in the range of about 140° C. to 200° C., and withdrawing as separate streams a concentrated liquid glycol phase containing at least about 99 weight percent glycol and a vaporous mixture containing water vapor from said second stage.

2. The method according to claim 1 wherein part of the liquid glycol phase withdrawn from the second stage is heated while flowing in a heat exchanger, and the resulting portion of said withdrawn glycol phase is returned to the second stage.

3. The method according to claim 2 wherein some of the partially concentrated glycol from the first stage and some of the concentrated liquid glycol phase from the second stage are each circulated through a respective heat exchanger, and both heat exchangers are heated in a reboiler with a single source of combustion gas.

4. The method according to claim 3 wherein stripping gas is fed to the second stage for supporting removal of water from said second stage.

5. The method according to claim 4 wherein the second stage is heated with preheated stripping gas.

6. The method according to claim 5 wherein the partially concentrated glycol is concentrated in the second stage in a packed column.

7. The method according to claim 6 wherein a pressure within the range of about 0.13 to 0.66 atm is used in the second stage.

8. The method according to claim 7 wherein the vaporous mixture which contains water vapour withdrawn from the second stage is cooled and is partially condensed, and the condensate is returned to the first stage.

9. The method according to claim 8 wherein the non-condensed part of the vapour is delivered as heating gas.

10. The method of claim 7 wherein a pressure within the range of about 0.33 to 0.46 atm is used in the second stage.

11. A method for concentrating a water-containing glycol selected from the group comprising diethylene glycol and triethylene glycol which has been used to dry natural gas and which contains from 92 to 95 percent glycol comprising treating the glycol in a first stage under glycol-concentrating and glycol-stable conditions including temperatures sufficient to vaporize and remove water from the water-containing glycol at atmospheric or superatmospheric pressures to thereby partially concentrate the glycol to form a glycol solution containing about 99 percent glycol, withdrawing as separate streams the partially concentrated glycol and a vaporous phase containing water vapor from said first stage, further concentrating said partially concentrated glycol in a second stage by vaporizing water from said glycol under glycol-concentrating and glycol-stable conditions including temperatures in the range of about 140° C. to 200° C. and subatmospheric pressures, withdrawing as separate streams a reconcentrated liquid glycol phase and a water vapor containing mixture from said second stage, heating a part of said glycol phase in a reboiler, and recycling the heated glycol phase to the second stage in order to maintain the temperature in said second stage within said 140° C. to 200° C. range.

12. The method of claim 11 wherein the glycol is diethylene glycol.

13. The method of claim 11 wherein the glycol is triethylene glycol.

* * * * *